(12) United States Patent
Sawada et al.

(10) Patent No.: US 7,619,220 B2
(45) Date of Patent: Nov. 17, 2009

(54) METHOD OF MEASURING ABERRATIONS AND CORRECTING ABERRATIONS USING RONCHIGRAM AND ELECTRON MICROSCOPE

(75) Inventors: Hidetaka Sawada, Tokyo (JP); Takumi Sannomiya, Kochi-Ken (JP)

(73) Assignee: JEOL Ltd., Tokyo (JP)

( * ) Notice: Subject to any disclaimer, the term of this patent is extended or adjusted under 35 U.S.C. 154(b) by 233 days.

(21) Appl. No.: 11/604,977

(22) Filed: Nov. 28, 2006

(65) Prior Publication Data
US 2007/0120055 A1 May 31, 2007

(30) Foreign Application Priority Data
Nov. 30, 2005 (JP) ............................. 2005-345538

(51) Int. Cl.
*G01N 23/00* (2006.01)
*G21K 7/00* (2006.01)
(52) U.S. Cl. .................. 250/311; 250/306; 250/307
(58) Field of Classification Search ................ 250/306, 250/307, 310, 311
See application file for complete search history.

(56) References Cited

U.S. PATENT DOCUMENTS

| | | | | |
|---|---|---|---|---|
| 6,541,779 B2 * | 4/2003 | Fujiwara | ...................... | 250/306 |
| 6,552,340 B1 | 4/2003 | Krivanek et al. | | |
| 6,628,845 B1 * | 9/2003 | Stone et al. | .................. | 382/294 |
| 2002/0126039 A1 * | 9/2002 | Dalton et al. | .................. | 342/26 |
| 2003/0001102 A1 | 1/2003 | Zach | | |
| 2004/0247244 A1 * | 12/2004 | Bao et al. | ...................... | 385/39 |
| 2005/0035293 A1 * | 2/2005 | Inada et al. | .................. | 250/311 |
| 2005/0189489 A1 * | 9/2005 | Moert et al. | ................. | 250/307 |
| 2005/0247884 A1 * | 11/2005 | Nakamura et al. | ...... | 250/396 R |
| 2008/0018893 A1 * | 1/2008 | Billard et al. | ................ | 356/338 |

OTHER PUBLICATIONS

Liang et al. "Interfacial reactions and thermal stability of ultrahigh vacuum deposited multilayered Mo/Si structures," Journal of Applied Physics. vol. 79. No. 8. pt 1, p. 4072-7. Published Apr. 15, 1996 in the USA, abstract attached from INSPEC.*
Taylor et al. "Fourier analysis of textural variations in human normal and cataractous lens nuclear fiber cell cytoplasm," Experimental Eye Research, 1999. vol. 69. N2, p. 163-174, abstract provided.*
Davatzikos et al. ("Spatial Normalization of Spine MR Images for Statistical Correlation of Lesions with Clinical Symptoms," Radiology, Sep. 2002, 224: 919-926 ).*
Javidi et al. ("Joint transform image correlation using a binary spatial light modulator at the Fourier plane," Applied Optics, Feb. 15, 1988, vol. 27. No. 4. ; pp. 663-665).*

* cited by examiner

*Primary Examiner*—Jack I Berman
*Assistant Examiner*—Brooke Purinton
(74) *Attorney, Agent, or Firm*—The Webb Law Firm (57) ABSTRACT

A method and apparatus for correcting aberrations using a Ronchigram. A STEM apparatus has first calculation means for taking autocorrelation of minute regions on a Ronchigram of an amorphous specimen, detection device for detecting aberrations in the beam formed from local angular regions on an aperture plane from the autocorrelation or from Fourier analysis of the autocorrelation, second calculation device for calculating the aberrations based on the results of the detection, and control device for controlling operation for correcting the aberrations based on results of calculations performed by the second calculation device.

8 Claims, 6 Drawing Sheets

METHOD OF MEASURING ABERRATIONS AND CORRECTING ABERRATIONS USING RONCHIGRAM AND ELECTRON MICROSCOPE

BACKGROUND OF THE INVENTION

1. Field of the Invention

The present invention relates to an electron microscope for imaging a specimen by focusing an electron beam (hereinafter may be referred to as the "electron probe" or simply as the "probe") onto the specimen, scanning the probe over the specimen, detecting the electrons transmitted through the specimen by an electron detector, and visualizing the output signal from the detector in synchronism with the electron beam scanning. More particularly, the invention relates to a method of measuring aberrations by an electron microscope equipped with an illumination system aberration corrector by the use of a Ronchigram and to a method and apparatus for correcting aberrations.

2. Description of Related Art

In transmission electron microscopy, a method of imaging a specimen by focusing an electron beam onto the specimen, scanning the beam over the specimen, detecting the electrons transmitted through the specimen by an electron detector, and displaying the output signal from the detector as a visible image in synchronism with the electron beam scanning is known as STEM (scanning transmission electron microscopy) imaging. The spatial resolution of STEM images is affected by various aberrations in the electron beam hitting the specimen. In recent years, apparatus capable of obtaining smaller electron beam diameters than heretofore have been put into practical use by incorporating an aberration corrector into the illumination system, the corrector being capable of correcting spherical aberration. The following two methods are known to measure aberrations in electron beams in such apparatus.

1) Method of correcting aberrations using a probe profile calculated by Fourier analysis. An image of a just focus and an underfocused (or overfocused) image are taken from dark field images of a reference specimen of gold particulates on the order of nanometers. A probe profile is calculated from the image of the just focus and from the underfocused or overfocused image by Fourier analysis, and aberrations are estimated. Parameters of various deflection systems and a stigmator are varied from the estimated aberrations, thus correcting the aberrations. This method uses no Ronchigram. The Ronchigram is an image of a specimen projected to an infinitely distant point as viewed from the specimen (back focal plane) by means of an electron beam focused onto the specimen in the STEM imaging mode.

2) A Ronchigram of a reference specimen (particulates of gold) is created and observed. Aberrations are calculated from variations in magnification caused by positional shift across the Ronchigram (in a quite small angular region). When the variations in the magnification due to shifting are calculated, the electron beam is moved across the specimen. The amount of movement of the Ronchigram made between, before and after the movement of the beam is used. The parameters of the systems of deflection and a stigmator are varied using the calculated aberrations. In this way, the aberrations are corrected. This method uses a Ronchigram.

One known apparatus of this kind, for example, as described in U.S. Patent Application Pub. No. 2003/0001102 images an object by means of a beam of particles focused onto the object, recording the image, repeating the process steps carried out until the recording step using underfocused and overfocused beams, Fourier-transforming the images, dividing the Fourier transform of the overfocused image by the Fourier transform of a focused image, inverse transforming the quotient (result of the division), dividing the Fourier transform of the underfocused image by the Fourier transform of the focused image, inverse transforming the result of the division, determining a brightness profile of the probe (i.e., images of the light sources of overfocused and underfocused images), determining the asymmetry of the contour about the center of the image, the width of the contour (especially, the half value width), and/or the curvature of the contour about the center, and using the differences in the probe contour for the different parameters to determine the aberrations in the image.

Another known apparatus using a beam of charged particles, for example, as described in U.S. Pat. No. 6,552,340 is designed to minimize the optical aberrations and includes a source of the charged particles, a probe-forming system of charged-particle lenses, a plurality of two-dimensional detectors, a power supply, a computer, and preferred software. This apparatus automatically corrects aberrations.

The above-described known methods have the following problems.

Any method of the above-described techniques uses a reference specimen. Where an actual specimen is observed using this method, it is necessary to replace the specimen. Furthermore, in order to search for a desired specimen location to be observed, the operating mode may be switched from STEM mode to TEM mode. This induces drifts of varying extents in the systems of deflection and stigmator.

When a specimen is observed in practice, various aberrations which should have been corrected vary due to drift (i.e., timewise variations of the magnetic field produced by the lenses). There is the problem that ultrahigh-resolution images cannot be obtained due to the introduced aberrations.

SUMMARY OF THE INVENTION

The present invention has been made in view of the foregoing problems. It is an object of the present invention to provide a method of measuring aberrations using a Ronchigram of an amorphous portion (which may be on the order of nanometers long at an end of the specimen) actually present in a specimen in such a way that residual aberrations can be adjusted through observation of the Ronchigram.

It is another object of the present invention to provide method and apparatus of correcting aberrations using such a Ronchigram.

In an aberration corrector for use in an illumination system, the adjustive method for correcting aberrations is important. The shape of a Ronchigram is affected by residual aberrations. A human operator grasps the kinds of the residual aberrations by observing the Ronchigram and corrects the aberrations. Furthermore, a Ronchigram, i.e., shadow image, is captured, and the amounts and magnitudes of the aberrations are automatically calculated.

(1) A method of measuring aberrations according to a first embodiment of the present invention uses an electron microscope having a function of displaying an image of a specimen by focusing an electron beam onto the specimen, scanning the beam over the specimen, detecting electrons transmitted through the specimen by an electron detector, and visualizing the output signal from the detector in synchronism with the electron beam scanning. In this method, autocorrelation of local regions on a Ronchigram of an amorphous specimen is taken, and aberrations in the electron beam formed from local angular regions on the aperture plane are detected from the autocorrelation or from the Fourier transform of the autocorrelation. Based on the results of the detection, the aberrations are calculated.

(2) A method of measuring aberrations according to a second embodiment of the present invention is based on the first embodiment and further characterized in that a Gaussian function is used as a function representing the autocorrelation.

(3) A method of measuring aberrations according to a third embodiment of the present invention is based on the first embodiment and further characterized in that when the autocorrelation is analyzed, the isocontrast portion of the autocorrelation is fitted using an elliptical function.

(4) A method of measuring aberrations according to a fourth embodiment of the present invention is based on any one of the first through third embodiments and further characterized in that in order to find the absolute values of aberrations in the electron beam, parameters indicating variations in the aberrations in the electron beam are normalized using the amount of positional deviation from the focus occurring when the Ronchigram was obtained and the distance to a just focus.

(5) A method of measuring aberrations according to a fifth embodiment of the present invention is based on any one of the first through third embodiments and further characterized in that in order to find the absolute values of aberrations in the electron beam, two Ronchigrams are taken at different focal positions and that parameters indicating the aberrations in the electron beam are normalized using the differential distance between the focal positions.

(6) A method of measuring aberrations according to a sixth embodiment of the present invention is based on any one of the first through fifth embodiments and further characterized in that variations in geometrical aberrations caused when the energy of the electron beam directed at the specimen was varied are detected as variations in local regions of the Ronchigram and that a chromatic aberration coefficient is measured from the variation in the energy of the electron beam and from the amount of focal shift.

(7) A method of correcting aberrations according to a seventh embodiment of the present invention uses a method of measuring aberrations as set forth in any one of the first through sixth embodiments.

(8) An electron microscope according to an eighth embodiment of the present invention has a function of displaying an image of a specimen by focusing an electron beam onto the specimen, scanning the beam over the specimen, detecting electrons transmitted through the specimen by an electron detector and visualizing the output signal from the detector in synchronism with the electron beam scanning, and an aberration corrector for use in an illumination system. The electron microscope has first calculation device for taking autocorrelation of minute regions on a Ronchigram of the specimen that is amorphous, detection device for detecting aberrations in the electron beam formed from local angular regions on an aperture plane from the autocorrelation or from Fourier analysis of the autocorrelation, second calculation device for calculating aberrations based on results of the detection, and control device for the aberration corrector for correcting the aberrations based on results of calculations performed by the second calculation device.

According to the first embodiment, the aberrations can be automatically corrected using the Ronchigram.

According to the second embodiment, a Gaussian function can be used as a function representing the autocorrelation.

According to the third embodiment, the autocorrelation can be analyzed more precisely by fitting the isocontrast portion of the autocorrelation using an elliptical function.

According to the fourth embodiment, the absolute values of the aberrations in the electron beam can be found.

According to the fifth embodiment, the absolute values of the aberrations in the electron beam can be found.

According to the sixth embodiment, a chromatic aberration coefficient can be measured.

According to the seventh embodiment, the aberrations can be corrected.

According to the eighth embodiment, the aberrations can be corrected automatically using the Ronchigram.

Other objects and features of the invention will appear in the course of the description thereof, which follows.

DESCRIPTION OF THE PREFERRED EMBODIMENTS

Embodiments of the present invention are hereinafter described in detail with reference to the accompanying drawings.

Figure 1:
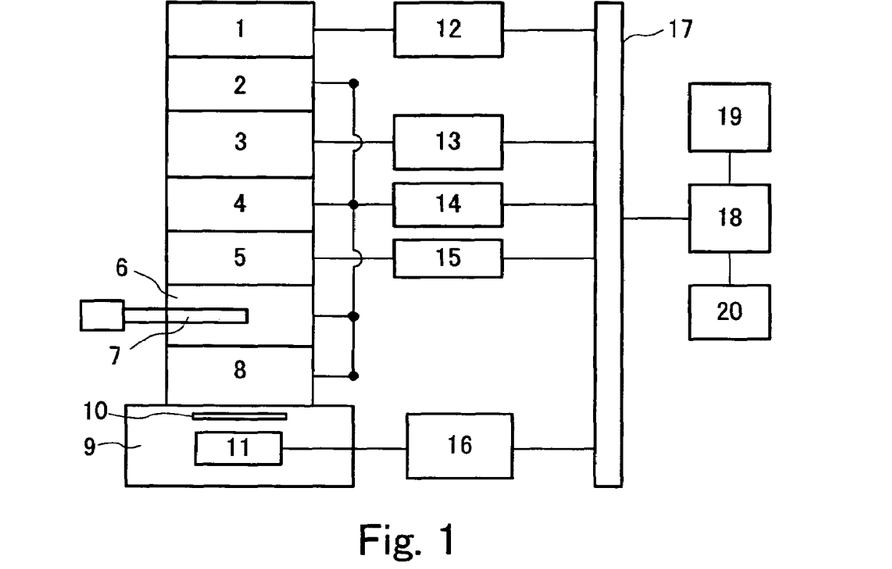
FIG. 1 is a block diagram showing an example of apparatus for implementing an embodiment of the present invention.

FIG. 1 is a block diagram showing an example of apparatus for implementing an embodiment of the present invention. The apparatus has an electron gun 1 for producing an electron beam, a first condenser lens 2 including a stigmator (i.e., astigmatism-correcting element), and an aberration corrector 3 incorporated in the illumination system and including a stigmator for correcting aberrations in the illumination system of the apparatus. The aberration corrector 3 of the illumination system includes electron beam-deflecting elements and the stigmator.

The apparatus further includes a second condenser lens 4 having deflectors, a scan assembly 5 for scanning an electron beam, an objective lens 6, a specimen stage 7, an imaging lens system 8 including intermediate and projector lenses, and an observation chamber 9 for observing a projected image. A projection screen 10 (removable) and a CCD camera 11 are equipped in the observation chamber 9.

The apparatus further includes a high-voltage controller 12 for applying a high voltage to the electron gun 1, an aberration correction controller 13 for controlling the aberration corrector 3, an amplifier 14 for driving a power supply to the lenses, scan controller 15 for controlling the scan assembly 5, and an image-processing device 16 for processing the image signals from the CCD camera 11, an interface 17, a computer 18, a display device 19, and an input device 20. A specimen (not shown) is held in the specimen stage 7. The operation of the apparatus constructed in this way is next described briefly.

The electron beam emitted from the electron gun 1 is focused by the first condenser lens 2, and astigmatic correction is performed. Then, the beam enters the aberration corrector 3 in the illumination system. In the aberration corrector 3, the beam is deflected in two dimensions, and corrections of aberrations including spherical aberration are made. The electron beam from the front focal point of the objective lens hits the specimen (not shown).

At this time, the electron beam transmitted through the specimen is focused at the back focal point of the objective lens 6 and then an image is projected onto the projection screen 10 in the observation chamber 9 via the imaging lens system 8. The operator can view alternatively the projected image on the projection screen 10 or taken image by the CCD camera 11 on the display device 19 and can operate the apparatus using the input device 20.

Figure 6:
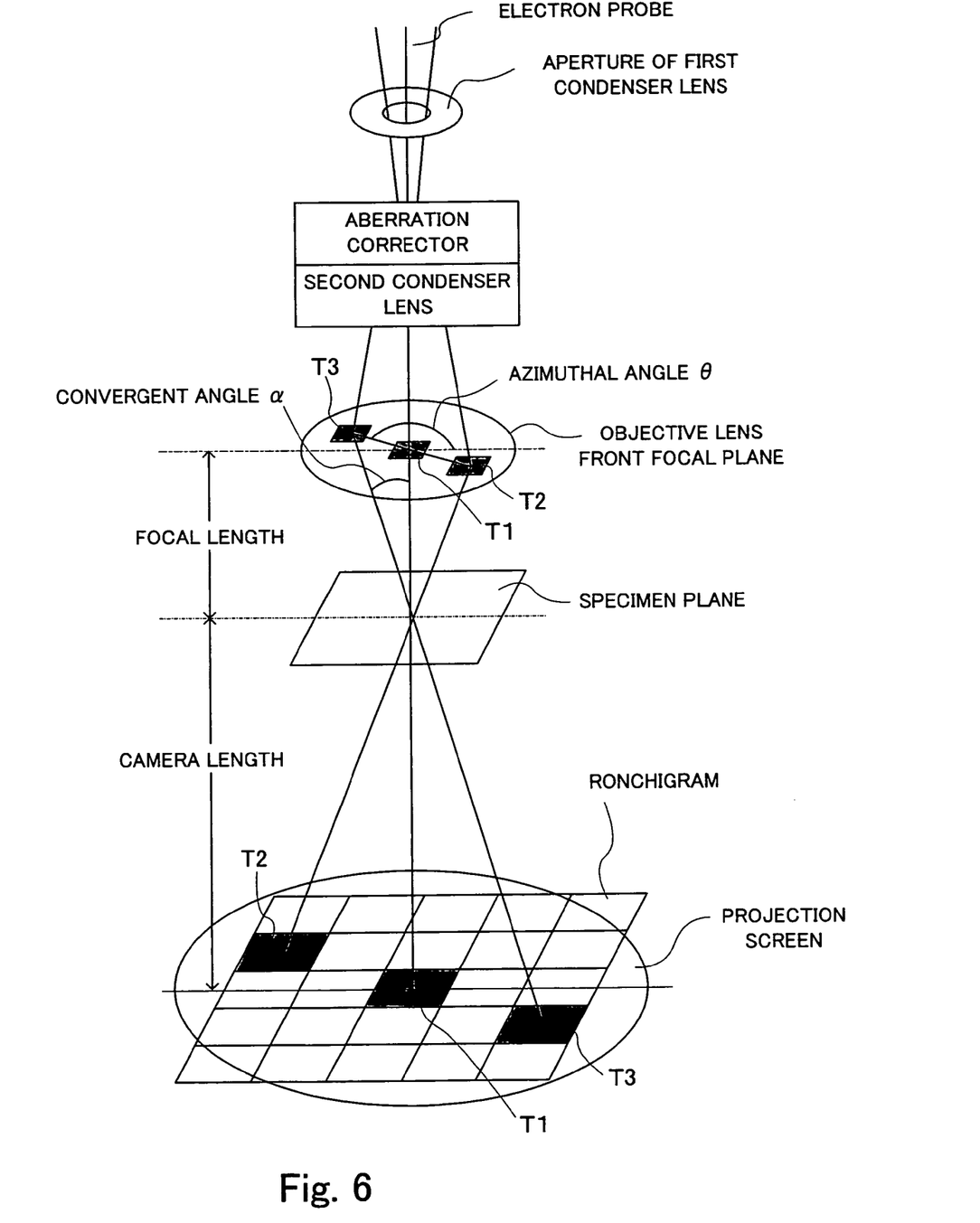
FIG. 6 is a diagram illustrating the relationship between aberrations in an electron probe and a Ronchigram.

The relation between aberrations in the electron probe and a Ronchigram is next described by referring to FIG. 6, where the angular space plane of the front focal plane (or aperture plane of the first condenser lens 2) of the objective lens 6 is referred to as the aperture plane. The angular space plane is denoted by convergent angle α and azimuthal angle θ. Certain angular regions on the aperture plane such as T1, T2, and T3 are referred to as the local angular regions on the aperture plane. A Ronchigram is observed on the projection screen 10 in the observation chamber 9. Figures at positions infinitely far apart from the specimen (corresponding to different angles of the probe) are projected onto the Ronchigram. There is a 1:1 relationship between each local angular region on the aperture plane and a corresponding local angular region on the Ronchigram.

Actual operation for correcting aberrations is next described. FIGS. 2a-2e illustrate processing for correction of aberrations, and shows half-toned images showing examples of the main window displayed on the viewing screen of a display unit in accordance with one embodiment of the present invention. FIGS. 3a-3f and FIG. 4 show similar images. A case in which manual operations are performed is first described. The operating mode of the apparatus is set to scanning transmission electron microscopy (STEM) mode to have a camera length and a scanning magnification permitting easy observation of the Ronchigram. Then, the apparatus is set to spot mode to stop the scanning of the electron beam. The beam is then moved to the amorphous portion at an end of the specimen to observe the Ronchigram.

Figure 2A:
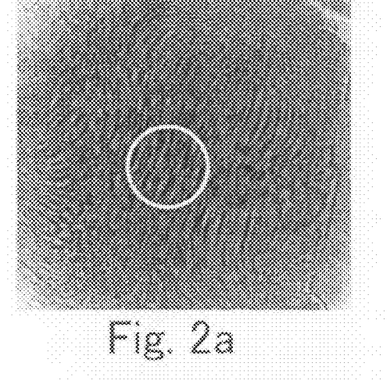
FIGS. 2a, 2b, 2c, 2d and 2e show diagrams illustrating processing for correcting aberrations.
Figure 2B:
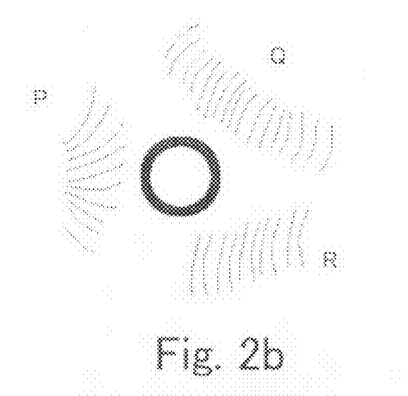

The beam is focused on the specimen by movement (Z motion) along the height of the specimen. The Ronchigram is observed. A pattern of lines is observed in the center indicated by a white circle as shown in FIG. 2a. This pattern is surrounded by patterns of radiating lines. Where the spherical aberration corrector consists of a hexapole element, the Ronchigram is made up of three (P, Q, and R) patterns of radiating lines or six patterns as shown in FIG. 2b. Generally, where there is a spherical aberration corrector, a Ronchigram consisting of multiple patterns of radiating lines is observed.

Figure 2C:
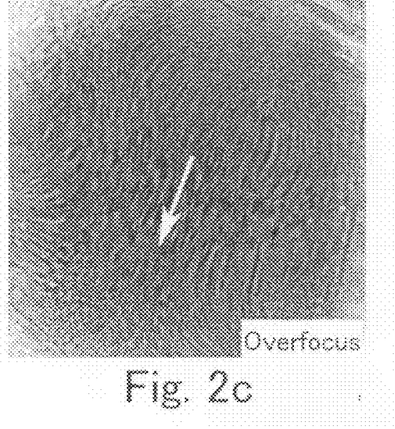
Figure 2D:
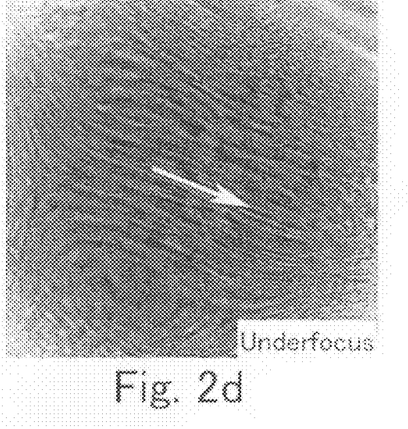
Figure 2E:
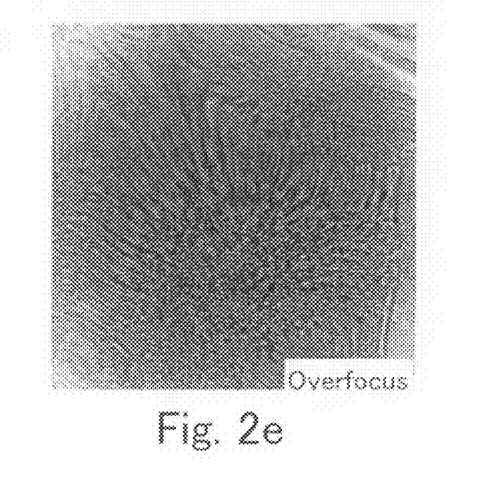
Figure 3A:
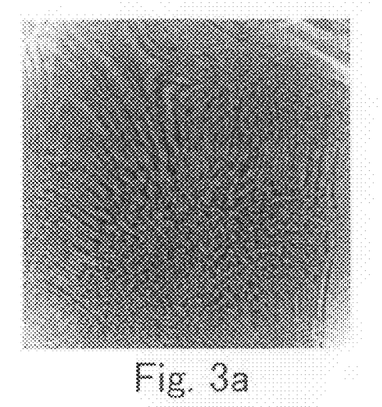
FIGS. 3a, 3b, 3c, 3d, 3e and 3f show diagrams illustrating processing for correcting aberrations.
Figure 3B:
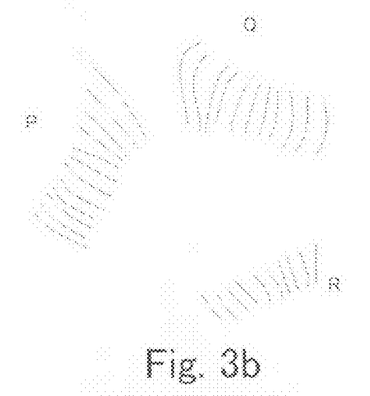
Figure 3C:
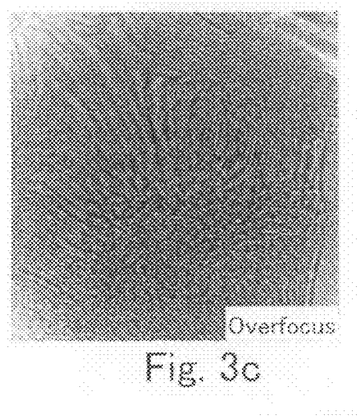
Figure 3D:
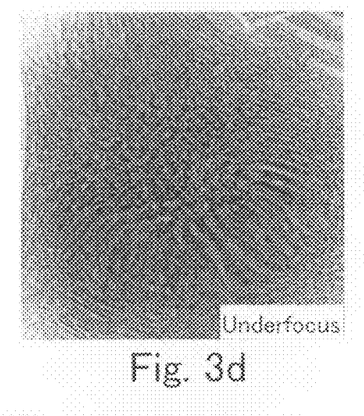
Figure 3E:
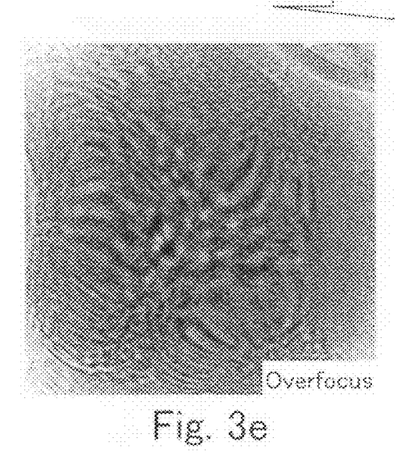
Figure 3F:
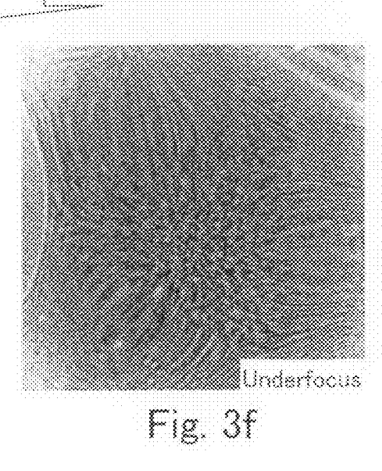

Lines located in the center and directed at a certain direction are eliminated using the stigmator coil. At this time, it is ascertained that the direction of the lines is inverted as shown in FIGS. 2c and 2d while varying the focus. In the final Ronchigram, there is no line having directionality in the center near the just focus as shown in FIG. 2e. Consequently, the two-fold astigmatism can be corrected.

Then, the deflection coil is adjusted such that the radiating lines of the patterns observed in peripheral portions become uniform in length as shown in FIGS. 3a-3f. As a result, the radiating lines vary from FIGS. 3a, to 3e or to 3f. Generally, coma can be corrected by adjusting the deflection coil such that all the patterns of radiating lines on the Ronchigram become uniform in geometry.

Figure 4:
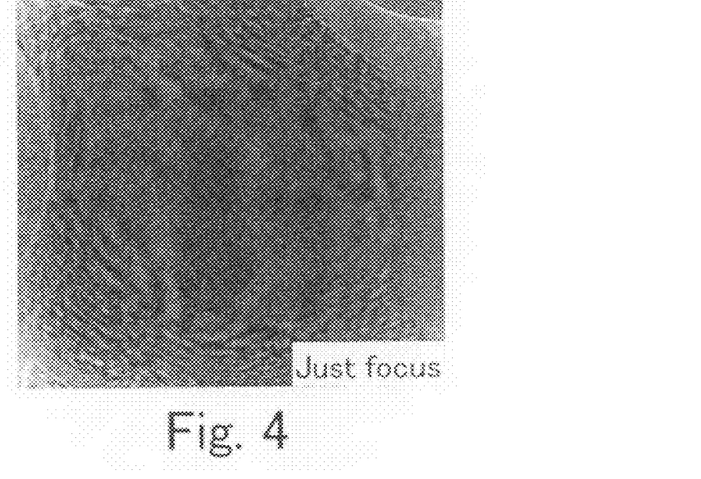
FIG. 4 is a diagram illustrating processing for correcting aberrations.

The processing illustrated in FIGS. 2a-2e and FIGS. 3a-3f is repeated a required number of times to obtain a Ronchigram in which the contrast in the central portion as described below is uniform at the just focus. FIG. 4 illustrates processing for correction of aberrations. When the aberrations have been corrected, the central region having no contrast is extended.

As described so far, the states of the various aberrations can be seen from variations in the Ronchigram of the amorphous portion of the specimen. In the present invention, the process steps described above are automated. Furthermore, aberrations up to higher orders can be calculated and corrected.

Figure 8:
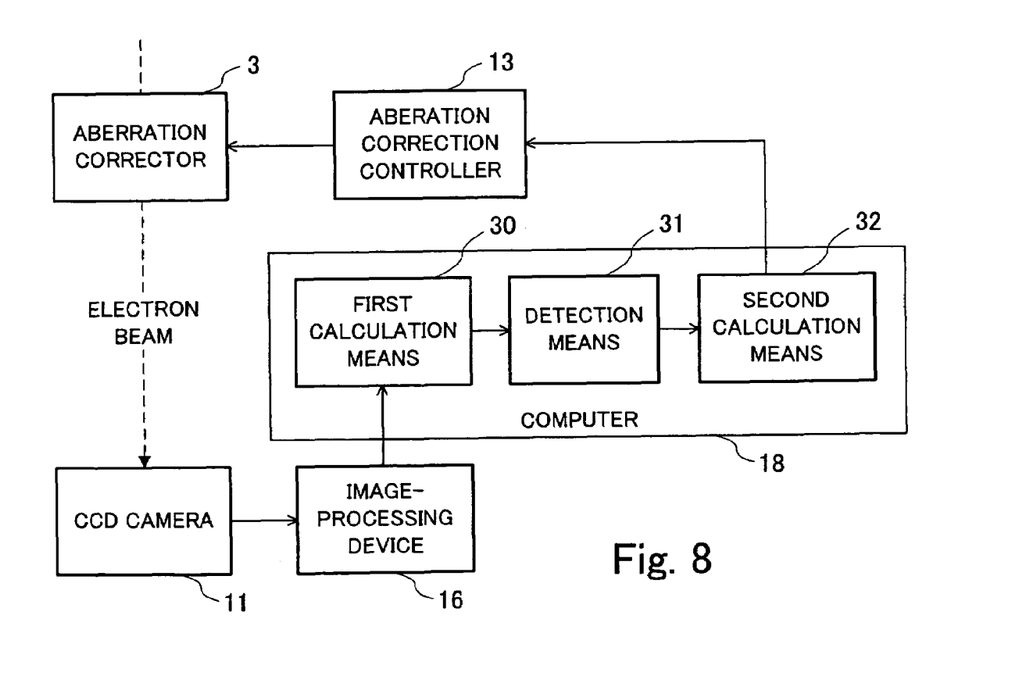
FIG. 8 is a block diagram showing an example of the device and process for implementing an embodiment of the present invention.

From image recognition of the Ronchigram, calculations of aberrations are performed as described below. The aberrations are corrected using the results of the calculations of the aberrations automatically. FIG. 8 is a block diagram showing an example of device and process for correcting the aberrations under computer control.

In FIG. 8, the computer 18 includes a first calculation device 30 for taking autocorrelation of minute regions on a Ronchigram of the specimen that is amorphous, a detection device 31 for detecting aberrations in the electron beam formed from local angular regions on an aperture plane from the autocorrelation or from Fourier analysis of the autocorrelation, and a second calculation device 32 for calculating aberrations based on results of the detection. The aberration correction controller 13 controls the aberration corrector 3 in the illumination system for correcting the aberrations based on results of calculations performed by the second calculation device 32.

In the method given below, aberration functions are found by finding derivatives of geometrical aberrations from autocorrelation functions of local regions of a Ronchigram. An aberration function χ referred to herein represents the sum of wavefront aberrations. In high-resolution electron microscopy, only on-axis aberrations are treated and so the following aberrations are discussed. Each aberration has an amplitude portion and an angular portion.

aberration function χ=focal shift+2-fold astigmatism+3-fold astigmatism+on-axis coma+spherical aberration+4-fold astigmatism+star aberration+5-fold astigmatism+three-lobe aberration+4th-order on-axis coma+5th-order spherical aberration+6-fold astigmatism . . . .

A method for taking autocorrelation of minute regions on a Ronchigram performed by the first calculation device 30 is next described.

Let $f$ be a function of interest. An autocorrelation function is given by Eq. (1) below.

$$\int f(s)\overline{f(s-x)}ds \tag{1}$$

An aberration function χ on an aperture plane is represented by a sum of wavefront aberration functions. Let G be a geometrical aberration. Let e1 and e2 be base vectors defining a two-dimensional space. Then, we have $$\vec{G} = (Ge1, Ge2) = \frac{\lambda}{2\pi}\left(\frac{\partial x}{\partial e1}, \frac{\partial x}{\partial e2}\right) \tag{2}$$

For example, (e1, e2) assumes the form (α, θ), (X, Y). Let P be a function indicating positional information about a specimen. A Ronchigram is given by P (Ge1, Ge2). Expanding Ge1 and Ge2 about eI and eII (where eI and eII are unit vectors in (α, θ), (X, Y) directions) in a two-dimensional plane gives rise to:

$$Ge1 = GeI + Ade1 + Bde2$$

$$Ge2 = GeII + Bde1 + Cde2$$

where $$A = \frac{\partial Ge1}{\partial e1}\bigg|_{eIeII}$$
$$B = \frac{\partial Ge1}{\partial e2}\bigg|_{eIeII}$$
$$C = \frac{\partial Ge2}{\partial e2}\bigg|_{eIeII}$$ (3)

Note that |eI, eII included in Eq. (3) means that the values of eI, eII are entered into e1 and e2 that are the results of partial derivatives. Functions are still left behind only if partial differentiation is performed and, therefore, the values of eI, eII are substituted into the variables of the function. In consequence, the values of A, B, and C are determined specifically.

Then, the variations in the aberrations in the electron beam are indicated by the variations in the unit vectors.

With respect to a specimen not dependent on position, such as an amorphous specimen, a Ronchigram is given by $$P(Ade1+Bde2, Bde1+Cde2)$$

In this way, in local regions of a Ronchigram, geometrical aberrations in an electron probe formed from local angular regions on the aperture plane can be seen.

A method for detecting aberrations in the electron beam formed from local angular regions on an aperture plane from the autocorrelation performed by the detection device 31 is next described. The probe profile (i.e., aberrations in the probe) can be found by Fourier analysis of the autocorrelation function. If an autocorrelation function of an image of an amorphous specimen is given by a Gaussian function, i.e., $$\exp\left(-\frac{((de1)^2 + (de2)^2)}{\sigma^2}\right)$$ (4)

an autocorrelation function in each local region on the Ronchigram is given by $$\exp\left(-\frac{((Ade1 + Dde2)^2 + (Bde1 + Cde2)^2)}{\sigma^2}\right)$$ (5)

Therefore, A, B, and C are measured by fitting $(Ade1+Bde2)^2+(Bde1+Cde2)^2$ from an autocorrelation diagram. In the description above, the autocorrelation function of the amorphous specimen image is a Gaussian function. It is not always necessary that the autocorrelation function be a Gaussian function. For example, when an autocorrelation is analyzed, the isocontrast portion of the autocorrelation diagram may be fitted using an elliptical function which results in:

$$(Ade1+Bde2)^2+(Bde1+Cde2)^2=K$$ (6)

where K is a constant.

Figure 5A:
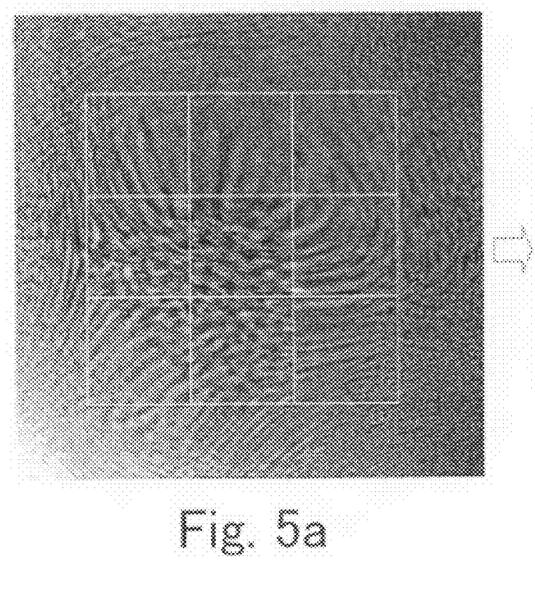
FIGS. 5a and 5b show an actually obtained Ronchigram and an autocorrelation diagram.
Figure 5B:
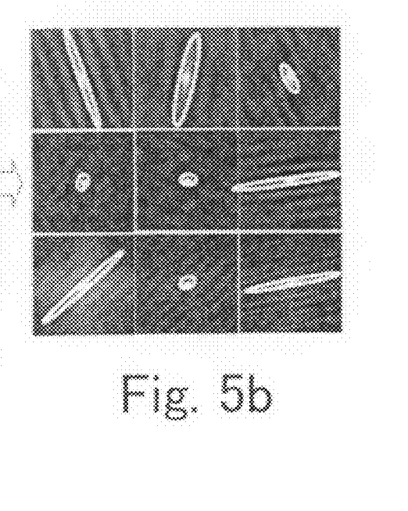
Figure 7:
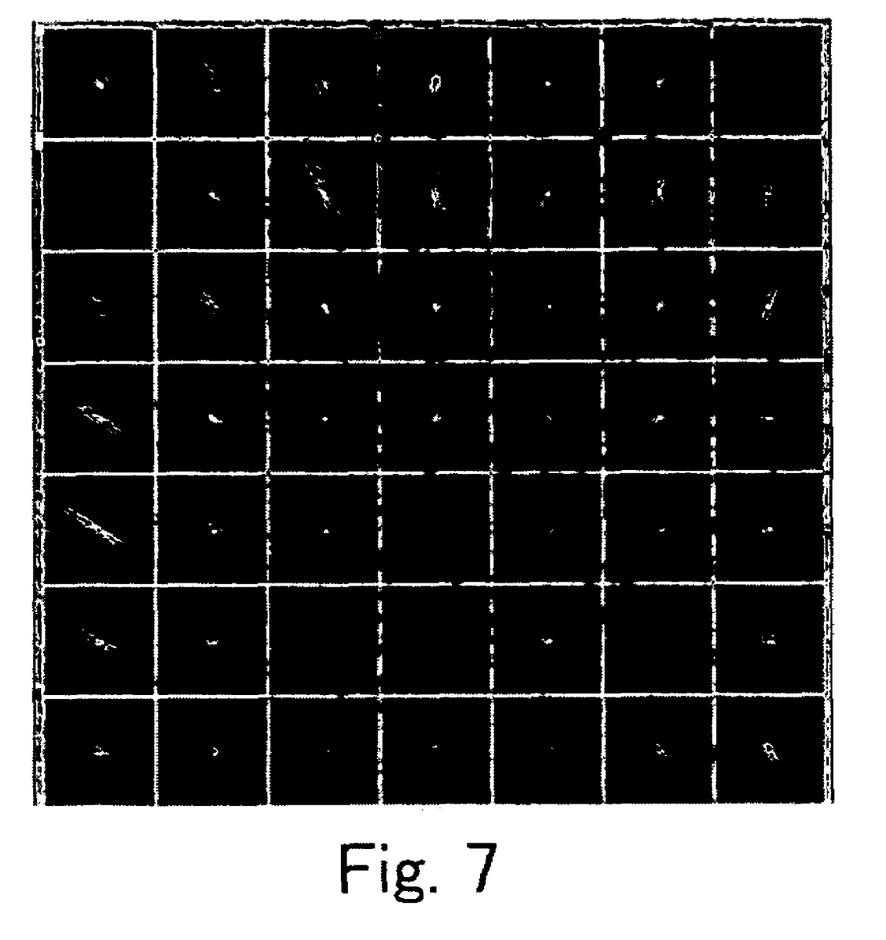
FIG. 7 shows an example of autocorrelation diagram, and in which a Ronchigram is divided into 7×7 parts.

A method for calculating aberrations performed by the second calculation device 32 based on results of the detection is next described. FIGS. 5a and 5b show an actual Ronchigram and an autocorrelation diagram. As shown in FIG. 5a, the whole area of the Ronchigram is divided into local regions. In the illustrated example, the whole area is divided into 3×3 small regions. FIG. 5b shows the autocorrelation function in the local regions shown in FIG. 5a and an example of fitting them. In FIG. 5b, elliptical white lines indicate that the portions are isocontrast portions. A, B, and C are found from the direction and size of the portion surrounded by each white line. To improve the correction accuracy, the whole Ronchigram is divided into about 7×7 small regions as shown in the example of fitting of FIG. 7 in many practical applications.

A, B, and C are measured from the autocorrelation functions in the local regions of the Ronchigram. When A, B, and C are measured, the autocorrelation function given in Eq. (1) is used. The absolute values of A, B, and C can be found by performing normalization by the amount of focal shift from the just focus, for example, when a Ronchigram is obtained. The normalization is equivalent to determining σ included in Eq. (5) in a case where a Gaussian function is used as an autocorrelation function. In the method of fitting the isocontrast portion of an autocorrelation diagram using an elliptical function, the normalization is equivalent to determining the constant K included in Eq. (6). Instead of the amount of focal shift from the just focus used for the normalization, the difference between the focal points of two Ronchigrams may be used.

An aberration function is calculated using the results of some measurements of A, B, and C and the relationship given in Eq. (3).

Based on the calculated aberrations, each corrective element in the aberration corrector 3 is so energized by the aberration correction controller 13 as to cancel the aberrations. In this way, the aberrations are automatically corrected.

It is not always necessary that aberrations be automatically corrected under computer control according to the results of calculations. Alternatively, calculated aberrations or amounts of corrections based on the calculations may be displayed on a display device 19 included in the apparatus shown in FIG. 1 and the operator may perform corrective manipulations by using the input device 20 while watching the displayed results.

In the above description, a method of correcting geometrical aberrations in an electron probe formed from local angular regions on an aperture plane is described. The method is not always restricted to correction of geometrical aberrations. That is, variations in geometrical aberrations (focal shift) caused by varying the energy of the electron probe (accelerating voltage) directed at the specimen can be detected as variations in the local regions of the Ronchigram. Chromatic aberration coefficient Cc can be measured from the variation in the energy and from the amount of the focal shift, and also chromatic aberration can be corrected.

In this way, the present invention can offer a method of measuring aberrations by using observation of a Ronchigram of an amorphous portion (which may be several nanometers long at an end of a specimen) actually present in the specimen, the method being capable of adjusting residual aberrations. Also, method and apparatus of correcting aberrations using such a Ronchigram are offered.

Having thus described our invention with the detail and particularity required by the Patent Laws, what is desired protected by Letters Patent is set forth in the following claims.

The invention claimed is:

1. A method of measuring aberrations by the use of an electron microscope having a function of displaying an image of a specimen by focusing an electron beam onto the specimen, scanning the beam over the specimen, detecting electrons transmitted through the specimen by an electron detector, and visualizing the output signal from the detector in synchronism with the electron beam scanning, said method comprising the steps of:
   taking autocorrelation of local regions on a Ronchigram of the specimen that is amorphous;
   detecting aberrations in the electron beam formed from local angular regions on an aperture plane from the autocorrelation or from Fourier analysis of the autocorrelation; and
   calculating the aberrations based on results of the detection.

2. A method of measuring aberrations as set forth in claim 1, wherein a Gaussian function is used as a function representing said autocorrelation.

3. A method of measuring aberrations as set forth in claim 1, wherein when said autocorrelation is analyzed, an isocontrast portion of said autocorrelation is fitted using an elliptical function.

4. A method of measuring aberrations as set forth in any one of claims 1 to 3, wherein parameters indicating variations in the aberrations in the electron beam are normalized using an amount of positional deviation from a focal point when said Ronchigram is derived and a distance to a just focus, in order to find absolute values of the aberrations in the electron beam.

5. A method of measuring aberrations as set forth in any one of claims 1 to 3, wherein two Ronchigrams providing different focal points are obtained and parameters indicating variations in the aberrations in the electron beam are normalized using the differential distance between the focal points, in order to find absolute values of the aberrations in the electron beam.

6. A method of measuring aberrations as set forth in any one of claims 1 to 3, wherein variations in geometrical aberrations caused when energy of the electron beam directed at the specimen are detected as variations in local regions of the Ronchigram, and a chromatic aberration coefficient is measured from a variation in the energy of the electron beam and from an amount of focal shift.

7. A method of correcting aberrations using a method of measuring aberrations as set forth in any one of claims 1 to 3.

8. An electron microscope having a function of displaying an image of a specimen by focusing an electron beam onto the specimen, scanning the beam over the specimen, detecting electrons transmitted through the specimen by an electron detector and visualizing the output signal from the detector in synchronism with the electron beam scanning, and an aberration corrector for use in an illumination system, said electron microscope comprising:
   first calculation means for taking autocorrelation of minute regions on a Ronchigram of the specimen that is amorphous;
   detection means for detecting aberrations in the electron beam formed from local angular regions on an aperture plane from the autocorrelation or from Fourier analysis of the autocorrelation;
   second calculation means for calculating aberrations based on results of the detection; and
   control means for the aberration corrector in the illuminating system for correcting the aberrations based on results of calculations performed by the second calculation means.

* * * * *